US007429680B2

(12) United States Patent
Siskin et al.

(10) Patent No.: US 7,429,680 B2
(45) Date of Patent: Sep. 30, 2008

(54) SYNTHESIS OF STERICALLY HINDERED SECONDARY AMINOETHER ALCOHOLS

(75) Inventors: Michael Siskin, Randolph, NJ (US); Alan Roy Katritzky, Gainesville, FL (US); Kostyantyn Mykolayevich Kirichenko, Gainesville, FL (US)

(73) Assignee: Exxonmobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 10/587,206

(22) PCT Filed: Feb. 1, 2005

(86) PCT No.: PCT/US2005/003052

§ 371 (c)(1), (2), (4) Date: Jun. 5, 2007

(87) PCT Pub. No.: WO2005/081777

PCT Pub. Date: Sep. 9, 2005

(65) Prior Publication Data

US 2007/0219400 A1 Sep. 20, 2007

Related U.S. Application Data

(60) Provisional application No. 60/545,118, filed on Feb. 17, 2004.

(51) Int. Cl.
C07C 209/00 (2006.01)
C07C 213/00 (2006.01)
C07C 213/02 (2006.01)
C07C 213/08 (2006.01)

(52) U.S. Cl. .............. 564/468; 564/506; 564/507; 564/508

(58) Field of Classification Search .............. 564/468, 564/506, 507, 508
See application file for complete search history.

(56) References Cited

U.S. PATENT DOCUMENTS

| 4,112,051 A | 9/1978 | Sartori et al. |
| 4,112,052 A | 9/1978 | Sartori et al. |
| 4,405,585 A | 9/1983 | Sartori et al. |
| 4,417,075 A | 11/1983 | Stogryn |
| 4,471,138 A | 9/1984 | Stogryn |
| 4,487,967 A | 12/1984 | Stogryn et al. |
| 4,508,692 A | 4/1985 | Savage et al. |
| 4,618,481 A | 10/1986 | Heinzelmann et al. |
| 4,665,234 A * | 5/1987 | Stogryn ............ 564/483 |
| 4,892,674 A | 1/1990 | Ho et al. |
| 4,894,178 A | 1/1990 | Ho et al. |
| 4,961,873 A | 10/1990 | Ho et al. |
| 5,098,604 A | 3/1992 | Brouard et al. |
| 5,874,623 A | 2/1999 | Adkins et al. |

FOREIGN PATENT DOCUMENTS

| GB | 2 017 524 | 10/1979 |
| WO | WO 2005/082835 | 9/2005 |
| WO | WO 2005/082836 | 9/2005 |
| WO | WO 2005/082837 | 9/2005 |

OTHER PUBLICATIONS

Frazier and Kohl, "Selective Absorption of Hydrogen Sulfide from Gas Streams", Industrial and Engineering Chemistry, Nov. 1950, pp. 2288-2292, vol. 42, No. 11, The Fluor Corporation Ltd., Los Angeles, California.
Overberger and Sarlo, "Mixed Sulfonic-Carboxylic Anhydrides", J. Am. Chem. Soc., Mar. 4, 1963, pp. 2446-2448, vol. 85.
Karger and Mazur, "Cleavage of Ethers by Mixed Sulfonic-Carboxylic Anhydrides", J. Am. Chem. Soc., Jul. 3, 1968, pp. 3878-3879, 90:14.

* cited by examiner

*Primary Examiner*—Peter G O'Sullivan
(74) *Attorney, Agent, or Firm*—Paul E. Purwin

(57) ABSTRACT

Severely sterically hindered secondary aminoether alcohols are prepared by reacting an organic carboxylic acid or alkali metal salt of an organic carboxylic acid with a sulfonyl halide, a sulfuryl halide, a mixed sulfuryl ester halide or a mixed sulfuryl amide halide to yield a sulfonic-carboxylic anhydride compound which is then reacted with a dioxane to cleave the ring of the dioxane, yielding a cleavage product which cleavage product is then aminated with an alkylamine and hydrolyzed with base to yield the severely sterically hindered secondary aminoether alcohol.

13 Claims, No Drawings

SYNTHESIS OF STERICALLY HINDERED SECONDARY AMINOETHER ALCOHOLS

This application is the U.S. National Phase filing of PCT Application No. PCT/US2005/003052 filed Feb. 1, 2005, which claims priority to U.S. Provisional Patent Application No. 60/545,118 filed Feb. 17, 2004.

FIELD OF THE INVENTION

The present invention relates to a method for the preparation of severely sterically hindered secondary aminoether alcohols which are useful in the removal of hydrogen sulfide from gaseous streams containing hydrogen sulfide and which may also contain carbon dioxide.

DESCRIPTION OF RELATED ART

It is well-known in the art to treat gases and liquids, such as mixtures containing acidic gases including $CO_2$, $H_2S$, $CS_2$, HCN, COS and oxygen and sulfur derivatives of $C_1$ to $C_4$ hydrocarbons with amine solutions to remove these acidic gases. The amine usually contacts the acidic gases and the liquids as an aqueous solution containing the amine in an absorber tower with the aqueous amine solution contacting the acidic fluid countercurrently. Usually this contacting results in the simultaneous removal of substantial amounts of both the $CO_2$ and $H_2S$. U.S. Pat. No. 4,112,052, for example, utilizes a sterically hindered amine to obtain nearly complete removal of $CO_2$ and $H_2S$ acid gases. This process is particularly suitable for systems in which the partial pressures of the $CO_2$ and related gases are low. For systems where the partial pressure of $CO_2$ is high or where there are many acid gases present, e.g., $H_2S$, COS, $CH_3SH$, $CS_2$, etc., a process utilizing an amine in combination with a physical absorbent, referred to as a "non-aqueous solvent process" is practiced. Such a system is described in U.S. Pat. No. 4,112,051.

Selective removal of $H_2S$ from acid gas systems containing both $H_2S$ and $CO_2$, however, is very desirable. Such selective removal results in a relatively high $H_2S/CO_2$ ratio in the separated acid gas which facilitates the subsequent conversion of the $H_2S$ to elemental sulfur in the Claus process.

The typical reactions of aqueous secondary and tertiary amines with $CO_2$ and $H_2S$ can be represented as follows:

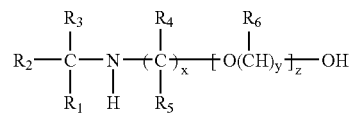

where R is the same or different organic radical and may be substituted with a hydroxyl group. Because the reactions are reversible they are sensitive to the $CO_2$ and $H_2S$ partial pressures which is determinative of the degree to which the reactions occur.

Selective $H_2S$ removal is particularly desirable in systems having low $H_2S/CO_2$ ratios and relatively low $H_2S$ partial pressures as compared to that of the $CO_2$. The ability of amine to selectivity remove $H_2S$ in such systems is very low.

Solutions of primary and secondary amines such as monoethanolamine (MEA), diethanolainne (DEA), diisopropanolamine (DPA), and hydroxyethoxyethylamine (DEA) absorb both $H_2S$ and $CO_2$, and thus have proven unsatisfactory for the selective removal of $H_2S$ to the exclusion of $CO_2$. The $CO_2$ forms carbamates with such amines relatively easily.

$H_2S$ has been selectively removed from gases containing $H_2S$ and $CO_2$ by use of diisopropanolamine (DIPA) either alone or mixed with a non-aqueous physical solvent such as sulfolane. Contact times, however, must be kept short to take advantage of the faster reaction of $H_2S$ with the amine as compared to the rate of $CO_2$ reaction with the amine.

Frazier and Kohl, Ind. and Eng. Chem., 42, 2288 (1950) showed that the tertiary amine methydiethanolamine (MDEA) is more selective toward $H_2S$ absorption as compared to $CO_2$. $CO_2$ reacts relatively slowly with tertiary amines as compared to the rapid reaction of the tertiary amine with $H_2S$. However, it has the disadvantage of having a relatively low $H_2S$ loading capacity and limited ability to reduce the $H_2S$ content to the desired level at low $H_2S$ pressures encountered in certain gases.

UK Patent Publication No. 2,017,524A discloses the use of aqueous solutions of dialkylmonoalkanolamines, e.g., diethylmonoethanol amine (DEAE), for the selective removal of $H_2S$, such material having higher selectivity and capacity for $H_2S$ removal at higher loading levels than MDEA. DEAE, however, has the disadvantage of a low boiling point of 161° C., making it relatively highly volatile resulting in large material loss.

U.S. Pat. No. 4,471,138 the entire teaching of which is incorporated herein by reference, teaches severely sterically hindered acyclic secondary aminoether alcohols having a high selectivity for $H_2S$ compared to $CO_2$. Selectivity is maintained at high $H_2S$ and $CO_2$ loadings.

The severely sterically hindered acyclic amine ether alcohols of U.S. Pat. No. 4,471,138 are represented by the general formula:

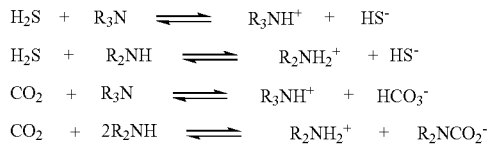

wherein $R_1$ and $R_2$ are each independently selected from the group consisting of alkyl and hydroxyalkyl radicals having 1-4 carbon atoms, $R_3$, $R_4$, $R_5$ and $R_6$ are each independently selected from the group consisting of hydrogen, alkyl, and hydroxyalkyl radicals having 1-4 carbon atoms, with the proviso that at least one of $R_4$ or $R_5$ bonded to the carbon atom which is directly bonded to the nitrogen atom is an alkyl or hydroxyalkyl radical when $R_3$ is hydrogen, x and y are each positive integers ranging from 2-4, and z is a positive integer ranging from 1-4. These materials are prepared by a high temperature reaction preferably in the presence of a solvent, of a secondary or tertiary alkyl primary amine with an ether alcohol containing a carbonyl functionality in the presence of a source of hydrogen or with a haloalkoxyalkanol. Preferably the composition is of the general formula:

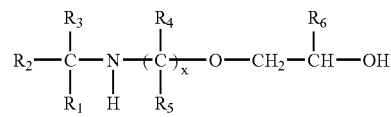

wherein:
$R_1=R_2=R_3=CH_3-$; $R_4=R_5=R_6=H$;

$R_1=R_2=R_3=CH_3—$; $R_4=H$ or $CH_3$; $R_5=R_6=H$;
$R_1=R_2=R_3=R_6=CH_3—$; $R_4=R_5=H$;
$R_1=R_2=R_3=CH_3CH_2—$; $R_4=R_5=R_6=H$; or
$R_1 \neq R_2 \neq R_3=H$, $CH_3—$, $CH_3CH_2—$; $R_4 \neq R_5 \neq R_6=H$, $CH_3—$;
and where x=2 or 3.

U.S. Pat. No. 4,487,967 is directed to a process for preparing severely sterically hindered secondary aminoether alcohols by reacting a primary amino compound with a polyalkenyl ether glycol in the presence of a hydrogenation catalyst at elevated temperatures and pressures. The primary amino compounds employed have a general formula:

where $R^1$ is selected from the group consisting of secondary or tertiary alkyl radicals having 3 to 8 carbon atoms or cycloalkyl radicals having 3 to 8 carbon atoms. The polyalkenyl ether glycols employed have the general formula:

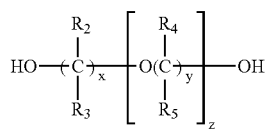

where $R_2$, $R_3$, $R_4$ and $R_5$ are each independently selected from the group consisting of hydrogen, $C_1$-$C_4$ alkyl radicals, and $C_3$-$C_8$ cycloalkyl radicals, with the proviso that if the carbon atom of $R_1$ directly attached to the nitrogen atom is secondary, at least one of $R_2$ and $R_3$ directly bonded to the carbon which is bonded to the hydroxyl group is as alkyl or cycloalkyl radical, x and y are each positive integers independently ranging from 2 to 4 and z is from 1 to 10, preferably 1 to 6, more preferably 1 to 4. The process is carried out in the presence of a catalytically effective amount of a supported Group VIII metal containing hydrogenation catalyst at elevated temperatures and pressure and the mole ratio of amino compound to polyalkenyl ether glycol is less than 2:1 when z is greater than 1.

SUMMARY OF THE INVENTION

A new process is disclosed for the production of severely sterically hindered secondary aminoether alcohols of the general formula 1:

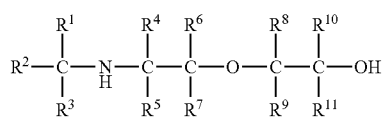

wherein $R^1$ and $R^2$ are each independently selected from the group consisting of alkyl and hydroxyalkyl radicals having 1 to 4 carbon atoms, preferably 1 to 2 carbon atoms, or $R^1$ and $R^2$ in combination with the carbon atom to which they are attached form a cycloalkyl group having 3 to 8 carbons; $R^3$ is selected from the group consisting of hydrogen, alkyl or hydroxyalkyl radicals having 1 to 4 carbon atoms, and mixtures thereof, preferably 1 to 2 carbon atoms, preferably alkyl or hydroxyalkyl radicals having 1 to 4 carbon atoms, more preferably 1 to 2 carbon atoms; $R^4$, $R^5$, $R^6$, $R^7$, $R^8$, $R^9$, $R^{10}$, and $R^{11}$ are the same or different and are selected from hydrogen, alkyl or hydroxyalkyl radicals having 1 to 4 carbon atoms, preferably 1 to 2 carbon atoms, or cycloalkyl radicals having 3 to 8 carbons; $R^4$, $R^5$, $R^6$, $R^7$, $R^8$, $R^9$, $R^{10}$, and $R^{11}$ are preferably hydrogen provided that when $R^3$ is hydrogen at least one of $R^4$ and $R^5$ bonded to the carbon directly bonded to the nitrogen atom is an alkyl or hydroxyalkyl radical. The process involves reacting an organic carboxylic acid or a salt of a carboxylic acid of the formula:

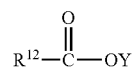

wherein $R^{12}$ is selected from the group consisting of alkyl radicals having 1 to 4 carbon atoms, preferably 1 to 2 carbon atoms, most preferably methyl, aryl radicals, substituted aryl radicals, preferably phenyl substituted with a hydrogen or one or more alkyl radicals having 1-10 carbon atoms, preferably 1-4 carbon atoms, most preferably methyl in the para position, and mixtures thereof, and Y is selected from the group consisting of hydrogen, alkali metal, ammonium, and mixtures thereof, preferably hydrogen or sodium, with a sulfonyl halide, a sulfuryl halide, a mixed sulfuryl ester halide, or a mixed sulfuryl amide halide of the formula:

wherein X is selected from the group consisting of F, Cl, Br, I, and mixtures thereof, preferably F, Cl, most preferably Cl, $R^{14}$ and $R^{14'}$ are the same or different and each is selected from the group consisting of alkyl radicals having 1 to 4 carbon atoms, preferably 1 to 2 carbon atoms, most preferably methyl, haloalkyl radicals of the formula $C_nH_{(2n+1)-w}Z_w$ wherein n is 1 to 4 preferably 1 to 2, and most preferably 1; Z is selected from the group consisting of F, Cl, Br, I, preferably F and Cl, most preferably F; and w ranges from 1 to 5, preferably 1 to 3, most preferably 3, aryl radicals 4

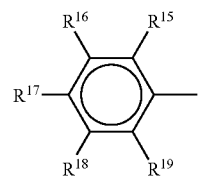

wherein $R^{15}$, $R^{16}$, $R^{17}$, $R^{18}$, and $R^{19}$ are the same or different and are selected from hydrogen and alkyl radicals having 1 to 20 carbon atoms, preferably $R^{15}$, $R^{16}$, $R^{18}$, and $R^{19}$ are hydrogen and $R^{17}$ is selected from hydrogen and an alkyl radicals having 1-4 carbons, preferably 1 to 2 carbons, more preferably methyl, and mixtures thereof, to yield sulfonic-carboxylic anhydride compounds of the formula 5:

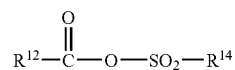

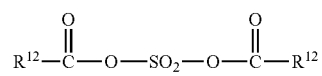

-continued

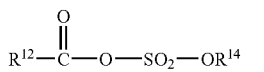

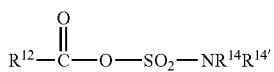

5c

5d which is then reacted with a dioxane of the formula 6:

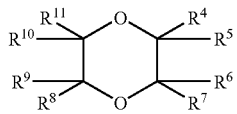

6 wherein $R^4$, $R^5$, $R^6$, $R^7$, $R^8$, $R^9$, $R^{10}$, and $R^{11}$ are the same or different and are selected from hydrogen, alkyl and hydroxyalkyl radicals having 1 to 4 carbons, preferably 1 to 2 carbons or cycloalkyl radicals having 3 to 8 carbons, more preferably $R^4$, $R^5$, $R^6$, $R^7$, $R^8$, $R^9$, $R^{10}$, and $R^{11}$ are hydrogen, to yield cleavage product materials of formula 7

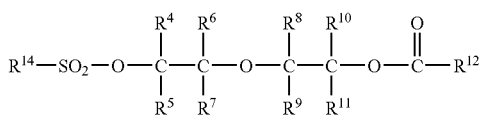

7a

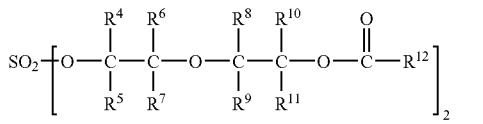

7b

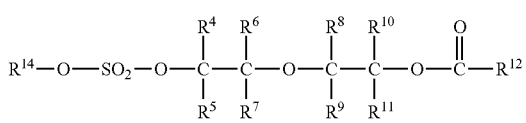

7c

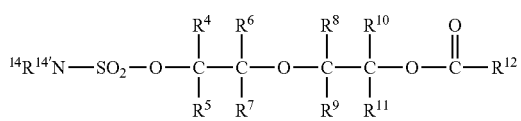

7d or mixtures thereof. It is not necessary that the product from each reaction step be isolated before being reacted with the reactant of a subsequent reaction step up to this point. A cleavage product is still produced The mixing of the organic carboxylic acid or salt thereof with a sulfonyl halide, sulfuryl halide, mixed sulfuryl ester halide or mixed sulfuryl amide halide and the dioxane can be in any order or sequence. Thus, the organic carboxylic acid or salt thereof can be mixed with the sulfonyl halide, etc. and then mixed with the dioxane, or the dioxane can be first mixed with the sulfonyl halide, etc. and then the organic carboxylic acid or salt thereof can be added, or the organic carboxylic acid or salt thereof and the dioxane can be mixed followed by the addition of the sulfonyl halide, etc. Thus, the combination of the organic carboxylic acid or salt thereof with the dioxane and the sulfonyl halide, sulfuryl halide, mixed sulfuryl ester halide or mixed sulfuryl amide halide can be combined into a single reaction mixture and reacted as a single mixture in the one step production of the desired cleavage product. This cleavage product is then reacted with an alkylamine of the formula 8:

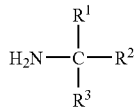

8 wherein $R^1$, $R^2$ and $R^3$ are as previously defined to yield 9

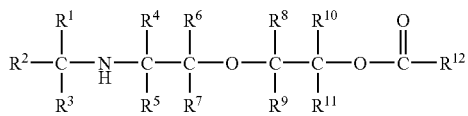

9 which is subsequently hydrolyzed with a base to yield 1

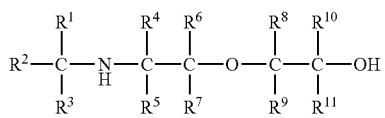

1

The preferred compounds defined by the general formula above include:

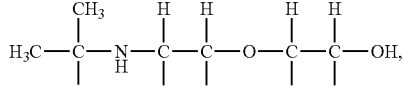

2-(2-tert-butylaminoethoxy)ethanol

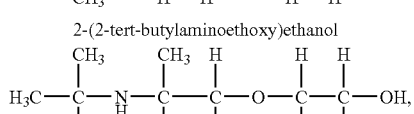

2-(2-tert-butylaminopropoxy)ethanol

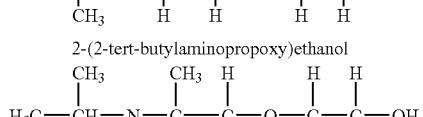

2-(2-isopropylaminopropoxy)ethanol

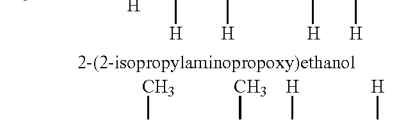

2-[2-(1,1-dimethylpropylamino)propoxy]ethanol

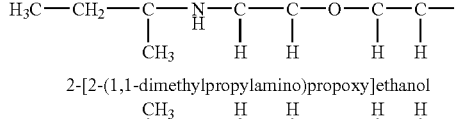

2-[2-(1,1-dimethylpropylamino)ethoxy]ethanol

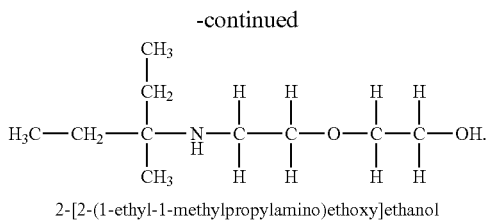

2-[2-(1-ethyl-1-methylpropylamino)ethoxy]ethanol

Typical starting materials to use as the first component are:

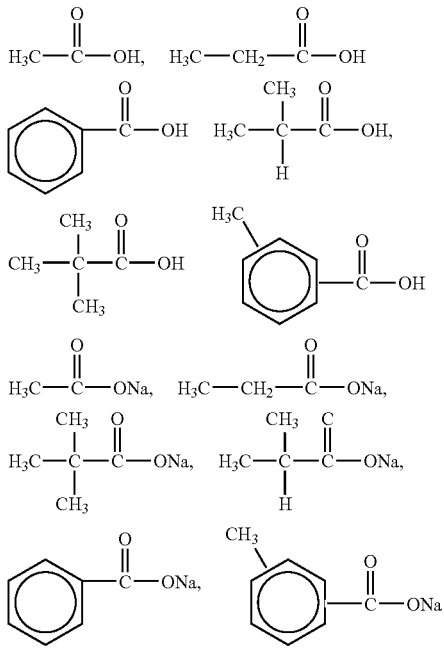

Other materials of the types described above can be readily envisioned.

This material is then is reacted with second component, typically

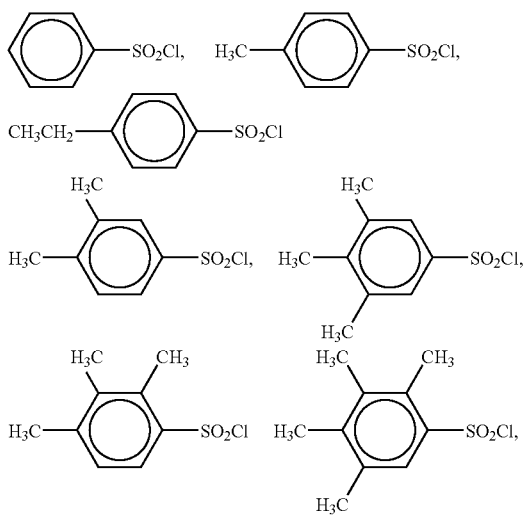

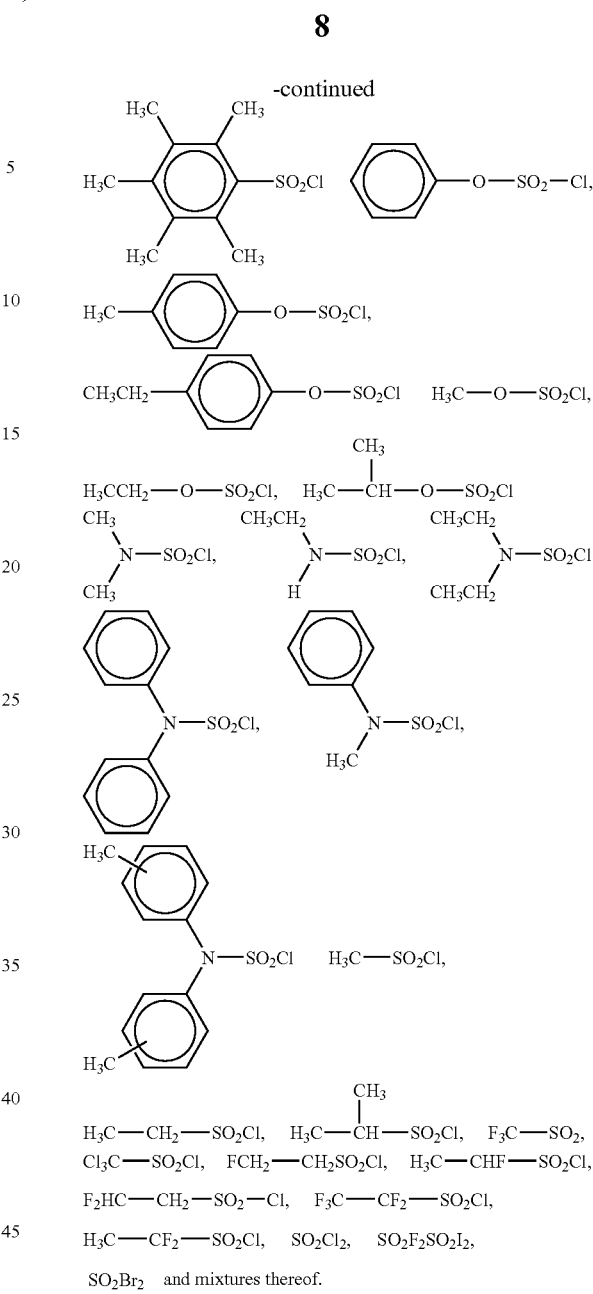

and mixtures thereof.

Similarly, other materials of the type described above can be readily envisioned.

The reaction of two such components yields acyl sulfonates 5a, 5b, 5c and 5d. The reaction can be conducted at a temperature in the range of between about −20 to 200° C., preferably about −20 to 150° C., more preferably about 0 to 120° C., and a pressure between about 1 bar to 100 bars, preferably about 1 bar to 50 bars, more preferably about 1 bar to 10 bars.

The reaction can be carried out neat, that is, in the absence of any solvent provided one or the other of the reactants in a liquid and capable of dissolving the non-liquid reactant, or both are liquid. Alternatively, an inert added solvent can be used such as sulfolane, hexanes or acetonitrile. Preferably the dioxane for the subsequent cleavage reaction is used as the solvent resulting in all three reactants being present in a unified first step wherein the reaction mixture contains the dioxane, organic carboxylic acid or salt thereof and the sulfonyl halide, sulfuryl halide, mixed sulfuryl ester halide or mixed sulfuryl amide halide. This reaction mixture can then be reacted under the conditions subsequently described for the dioxane cleavage reaction, yielding the cleavage product described by general formula 4.

The sulfonate 5a and/or 5b are reacted with a 1,4-dioxane, which is typically of the formula:

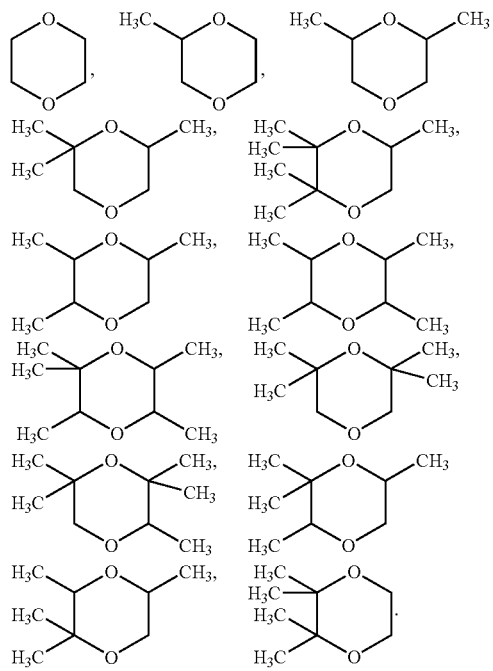

Other substituted isomers can be readily envisioned. Preferably, the 1,4-dioxane is

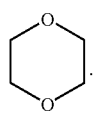

Reaction at elevated temperature is for a time sufficient to cleave the dioxane ring and to achieve about 60-90% conversion to cleavage product. The dioxane also serves as the solvent for the reaction. The molar ratio of dioxane to sulfonate can range from about 1:1 to about 10:1, preferably about 1:1 to about 8:1, most preferably about 1:1 to about 5:1. The reaction can be carried out in the absence of any added solvent, e.g., the dioxane serving as the solvent, or an additional solvent such as acetonitrile or toluene can be used, the reaction being conducted at temperatures between about 50° C. to about 200° C., preferably about 70° C. to about 160° C., more preferably about 80° C. to about 140° C.

Preferably, the reaction is carried out in the absence of any added solvent, the dioxane serving as both reactant and solvent, at a temperature in the range of about 50° C. to about 160° C., preferably about 70° C. to about 160° C., more preferably about 80° C. to about 140° C.

The dioxane cleavage step recited above are described in greater detail by Karger and Mazur in "The Cleavage of Ethers by Mixed Sulfonic-Carboxylic Anhydrides", Journal of the American Chemical Society, 1968, 90, 3878-3879. See also, "Mixed sulfonic-carboxylic anhydrides. I. Synthesis and thermal stability. New syntheses of sulfonic anhydrides" Journal of Organic Chemistry, 1971, 36, 528, and "Mixed sulfonic-carboxylic anhydrides. II. Reactions with aliphatic ethers and amines" Journal of Organic Chemistry, 1971, 36, 532.

The cleavage product 7a and/or 7b and/or 7c and/or 7d is then aminated with an amine 8 typically of the formula:

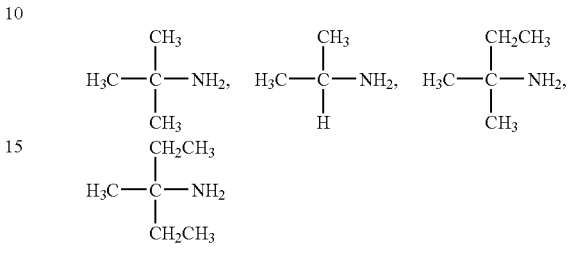

for a time sufficient to replace the $—O—SO_2—R^{14}$ or the sulfonate group in 7a and/or 7b and/or 7c and/or 7d by the amine 8. In the case of the amination of materials 7a, 7c and 7d, the amine to sulfonate group mole ratio is in the range of about 1:1 to about 10:1, preferably about 1:1 to about 8:1, more preferably about 1:1 to 4:1, while in the case of the amination of material 7b the amine to sulfonate group ratio is in the range of about 2:1 to about 10:1, preferably about 2:1 to about 8:1, more preferably about 2:1 to about 4:1. Expressed differently, in general the amine to group being replaced mole ratio can range from about stoichiometric to about 10:1, preferably about stoichiometric to about 8:1, more preferably about stoichiometric to about 4:1.

This amination step can be carried out under any conditions typical in the art. Amination can be conducted at atmospheric or at elevated pressure, elevated pressure being especially suitable when amination is performed using relatively low boiling amines such as t-butyl amine.

The amination can be conducted at pressures of from about atmospheric (1 bar) to about 100 bars, preferably about 1 to about 50 bars, and at temperatures of from about 40° C. to about 200° C., preferably about 40° C. to about 125° C. The amination can be performed using reflux, but this is not absolutely necessary. An inert solvent can be optionally used, such as benzene, toluene, diethyl ether, hexane, and the like.

Finally, the resultant 9

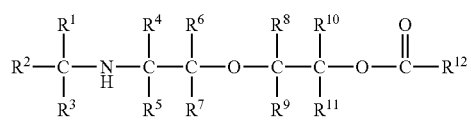

is hydrolyzed using a base to yield the final desired product 1. Typical bases include an alkali metal hydroxide, an alkali metal carbonate, or an alkali metal alkoxide, such as sodium hydroxide, sodium carbonate, sodium methoxide, sodium tert-butoxide, etc. Reaction is conducted at from about 20° C. to about 110° C., preferably about 20° C. to about 50° C. Reaction under reflux is effective and a desirable technique.

Use of a solvent is optional for the hydrolysis reaction, one being used if the reactants are not already in the liquid form. Solvents can include water, or alcohol and mixtures thereof.

If alcohols are used, they can be of the same carbon number or are the same alcohols from which the alkoxide bases themselves are derived. Thus, methanol would be a suitable solvent to use where the base is an alkali methoxide.

EXAMPLES

Cleavage with Methyl Acetyl Sulfate Generated in situ using Methyl Chlorosulfonate and Acetic Acid in the Presence of Triethylamine Methyl chlorosulfonate was prepared according to known procedure [Heller, M. S.; Lorah, D. P.; Cox, C. P., *Chem. Eng. Data*, 1983, 27, 134] by the reaction of sulfuryl chloride with methanol as follow: Methanol (15 g, 0.47 mol) was added dropwise to sulfuryl chloride at 0° C. (ice-bath cooling) and the reaction mixture was stirred at 0° C. for 3 hours. After evolution of hydrogen chloride ceased, the reaction mixture was distilled under reduced pressure to give methyl chlorosulfonate (23.5 g, 38%, bp 62° C./52-53 mm Hg; lit.[Heller, M. S.; Lorah, D. P.; Cox, C. P., *Chem. Eng. Data*, 1983, 27, 134] 55-56° C./39 mm Hg). $^1$H NMR (CDCl$_3$) δ4.21 (s, 3H); $^{13}$C NMR (CDCl$_3$) δ61.2

Cleavage of dioxane. A 25 mL one-necked flask was charged with acetic acid (0.97 mL, 1.0 g, 16.7 mmol), dioxane (7 mL, 7.0 g, 80 mmol), methyl chlorosulfonate (2.0 g, 15.3 mmol) and then with triethylamine (2.153 mL, 1.56 g, 15.3 mmol) at room temperature under nitrogen. The reaction mixture was refluxed for 72 h. The reaction progress was monitored by NMR. The reaction mixture was then evaporated under vacuum. Dry toluene (15 mL) and tert-butylamine (8.4 mL, 5.85 g, 80 mmol) were added to the residue and the mixture was gently refluxed for 24 hours. The reaction mixture was then cooled to room temperature and filtered. The solid was washed with toluene. The combined filtrate was evaporated under vacuum. The residue was extracted with toluene; the extract was filtered and evaporated under vacuum to give 0.3 g of brown oil. The NMR test showed the trace presence of desired product (t-BuNHCH$_2$CH$_2$OCH$_2$CH$_2$OAc). The signals in $^1$H NMR spectrum suggest the presence of acetates (HOCH$_2$CH$_2$OCH$_2$CH$_2$OAc) and/or (AcOCH$_2$CH$_2$OCH$_2$CH$_2$OAc).

The invention claimed is:

1. A method for the synthesis of severely sterically hindered secondary aminoether alcohols of the formula

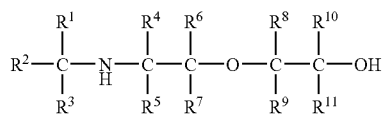

wherein $R^1$ and $R^2$ are each selected from the group consisting of alkyl, hydroxylalkyl radicals having 1 to 4 carbon atoms or in combination with the carbon atom to which they are attached they form a cycloalkyl group having 3 to 8 carbon atoms, and $R^3$ is selected from the group consisting of hydrogen, alkyl, hydroxyalkyl radicals having 1 to 4 carbon atoms, and mixtures thereof, and $R^4$, $R^5$, $R^6$, $R^7$, $R^8$, $R^9$, $R^{10}$ and $R^{11}$ are the same or different and are selected from the group consisting of hydrogen, alkyl and hydroxyalkyl radicals having 1 to 4 carbons provided that at least one of $R^4$ or $R^5$ bonded to the carbon atom directly bonded to the nitrogen atom is an alkyl or hydroxyalkyl radical when $R^3$ is hydrogen, the process involving reacting an organic carboxylic acid or salt of a carboxylic acid of the formula

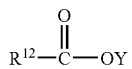

wherein $R^{12}$ is selected from the group consisting of alkyl radicals having 1 to 4 carbon atoms, aryl radicals bearing hydrogen or one or more $C_1$-$C_{10}$ alkyl groups substituted thereon, and mixtures thereof, and Y is selected from the group consisting of hydrogen, alkali metal, ammonium, and mixtures thereof, with a sulfonyl halide, a sulfuryl halide, a mixed sulfuryl ester halide, or a mixed sulfuryl amide halide of the formula

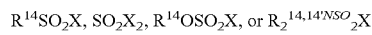

wherein X is selected from the group consisting of F, Cl, Br, I, and mixtures thereof, and $R^{14}$ and $R^{14'}$ are the same or different and each is selected from the group consisting of alkyl radicals having 1 to 4 carbon atoms, haloalkyl radicals of the formula $C_nH_{(2n+1)-w}Z_w$ wherein n is 1 to 4, Z is selected from the group consisting of F, Cl, Br, I, and mixtures thereof, and w ranges from 1 to 5, and aryl radicals

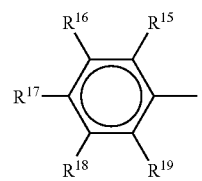

wherein $R^{15}$, $R^{16}$, $R^{17}$, $R^{18}$, and $R^{19}$ are the same or different and are selected from hydrogen and alkyl radicals having 1 to 20 carbon atoms, and mixtures thereof, to yield acyl sulfonate material of the general formula

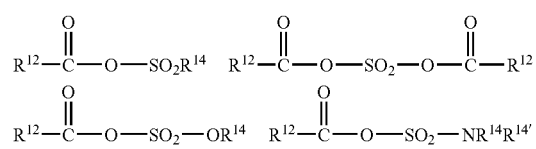

which is then reacted with a dioxane of the formula

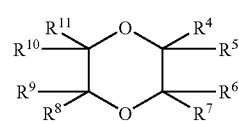

wherein $R^4$, $R^5$, $R^6$, $R^7$, $R^8$, $R^9$, $R^{10}$, and $R^{11}$ are the same or different and are selected from hydrogen, alkyl and hydroxyalkyl radicals having 1 to 4 carbons to yield

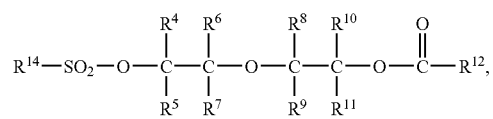

-continued

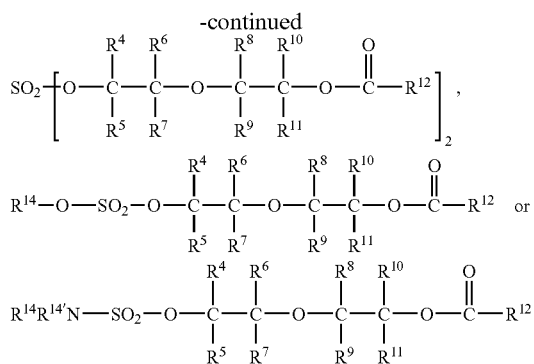

which is then aminated with an alkylamine of the formula

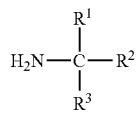

wherein $R^1$, $R^2$, and $R^3$ are as previously defined to yield

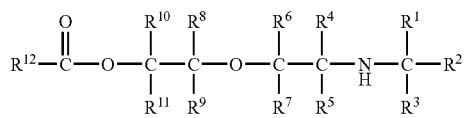

which is then hydrolyzed with base to yield

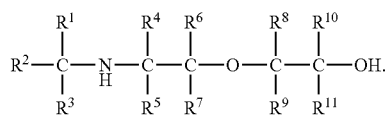

2. The method of claim 1 for the synthesis of severely sterically hindered secondary aminoether alcohols using sulfonyl halide of the formula $R^{14}SO_2X$.

3. The method of claim 1 for the synthesis of severely sterically hindered secondary aminoether alcohols using sulfuryl halide of the formula $SO_2X_2$.

4. The method of claim 1 for the synthesis of severely sterically hindered secondary aminoether alcohols using the mixed sulfuryl ester halide of the formula $R^{14}OSO_2X$.

5. The method of claim 1 for the synthesis of severely sterically hindered secondary aminoether alcohols using the mixed sulfuryl amide halide of the formula $R_2^{14,14'}NSO_2X$.

6. The method according to claim 1, 2, 3, 4 or 5 wherein $R^1$, $R^2$ and $R^3$ are methyl radicals.

7. The method according to claim 1, 2, 3, 4 or 5 wherein $R^4$, $R^5$, $R^6$, $R^7$, $R^8$, $R^9$, $R^{10}$, and $R^{11}$ are hydrogen.

8. The method according to claim 1, 2, 3, 4 or 5 wherein $R^{15}$, $R^{16}$, $R^{18}$, and $R^{19}$ are hydrogen and $R^{17}$ is hydrogen or methyl.

9. The method according to claim 1, 2, 3, 4 or 5 wherein the base is selected from alkali metal hydroxide, alkali metal alkoxide, or alkali metal carbonate.

10. The method according to claim 1, 2, 3, 4 or 5 wherein Y is hydrogen or sodium.

11. The method according to claim 1, 2, 3, 4 or 5 wherein $R^1$, $R^2$ and $R^3$ are methyl, $R^4$, $R^5$, $R^6$, $R^7$, $R^8$, $R^9$, $R^{10}$, and are hydrogen, $R^{15}$, $R^{16}$, $R^{18}$, and $R^{19}$ are hydrogen, $R^{17}$ is hydrogen or methyl, and Y is hydrogen, sodium, or ammonium.

12. The method according to claim 1, 2, 3, 4 or 5 wherein the acyl sulfonate is made by reacting organic carboxylic acid or the salt of a carboxylic acid with the sulfonyl halide, sulfuryl halide, mixed sulfuryl ester halide or mixed sulfuryl amide halide at a temperature in the range of between about −20 to 200° C. at a pressure between about 1 bar and 100 bars, the acyl sulfonate is reacted with the dioxane at a molar ratio of dioxane to acyl sulfonate in the range of 1:1 to 10:1 at a temperature of between about 50° C. to about 200° C. to yield a cleavage product, the cleavage product and the alkyl amine reacted at an amine to sulfonate group ratio ranging from about stoichiometric to about 10:1 at pressure of from about atmospheric (1 bar) to about 100 bars at temperature of from about 40° C. to about 200° C., and the resulting aminated product is hydrolyzed with base at a temperature from about 20° C. to about 110° C.

13. The method according to claim 1, 2, 3, 4 or 5 wherein the organic carboxylic acid or the salt thereof, the sulfonyl halide, sulfuryl halide, mixed sulfuryl ester halide or mixed sulfuryl amide halide and the dioxane care combined in a single step to produce a reaction mixture, the reaction mixture being heated at a temperature of between about 50° C. to about 200° C. to produce the cleavage product, the cleavage product and the alkylamine are reacted at am amine to cleavage product ratio ranging from about stoichiometric to about 10:1 at a pressure from about atmospheric (1 bar) to about 100 bars at a temperature of from about 40° C. to about 200° C., the resulting aminated product being reacted with base at a temperature from about 20° C. to about 110° C.

* * * * *